(12) United States Patent
Jacob et al.

(10) Patent No.: US 6,696,059 B2
(45) Date of Patent: Feb. 24, 2004

(54) COMBINATION DRUG THERAPY FOR GLYCOLIPID STORAGE DISEASES

(75) Inventors: Gary S. Jacob, St. Louis, MO (US); Raymond A. Dwek, Oxford (GB)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 10/054,802

(22) Filed: Jan. 22, 2002

(65) Prior Publication Data

US 2002/0127213 A1 Sep. 12, 2002

Related U.S. Application Data (63) Continuation-in-part of application No. 09/620,026, filed on Jul. 20, 2000.
(60) Provisional application No. 60/145,568, filed on Jul. 26, 1999.

(51) Int. Cl.[7] .......................... A61K 38/47; A01N 43/40
(52) U.S. Cl. ..................................... 424/94.61; 514/328
(58) Field of Search ..................... 514/328; 424/94.61

(56) References Cited

U.S. PATENT DOCUMENTS

| | | | |
|---|---|---|---|
| 5,030,638 A | | 7/1991 | Partis et al. |
| 5,472,969 A | | 12/1995 | Platt et al. |
| 5,705,153 A | * | 1/1998 | Shorr et al. |
| 5,786,368 A | | 7/1998 | Platt et al. |
| 5,798,366 A | | 8/1998 | Platt et al. |
| 5,801,185 A | | 9/1998 | Platt et al. |

FOREIGN PATENT DOCUMENTS

| | | | |
|---|---|---|---|
| EP | 0193770 | 2/1986 | ......... C07D/211/46 |
| WO | WO9802161 | 1/1998 | ......... A61K/31/445 |

OTHER PUBLICATIONS

Legler, G et al., Biol. Chem. Hoppe–Seyler (1985), 366(12): 1113–22. Glucosylceramidase from calf spleen. Characterization of its active site with 4–n–alkylumbelliferyl beta–glucosidases and N–alkyl derivatives of 1–deoxynojirimmycin.*
Beutler, Proc. Natl. Acad. Sc. USA 90, 5384–5390 (1993).
Dale & Beutler, Proc. Natl. Acad. Sc. USA 73, 4672–4674 (1976).
Beutler, Science 256, 794–799 (1992).
Platt et al., J. Biol. Chem. 269, 8362–8365 (1994).
Block et al., Nature Medicine 4, 610–614 (1998).
Platt et al., Trends in Glycoscience & Glycotech., vol. 7, No. 38, 495–511 (1995).
Platt et al., Biochem. Pharmacol. 56, 421–430 (1998).
Platt et al., J. Biol. Chem., 272, 19365–19372 (1997).
Cox et al., Lancet, vol. 355, 1481–1485 (2000).
Radin, Glycoconjugate J., vol. 13, 153–157 (1996).
Zitzmann et al., Proc. Natl. Acad. Sci. USA, vol. 96, 11878–11882 (1999).
Legler et al., Biol. Chem. Hoppe–Seyler (1985), 366 (12), 1113–22.

* cited by examiner

*Primary Examiner*—Christopher R. Tate
*Assistant Examiner*—Michele C. Flood
(74) *Attorney, Agent, or Firm*—Scott J. Meyer (57) ABSTRACT

A combination drug therapy is disclosed for the treatment of a patient affected with Gaucher's disease or other such glycolipid storage diseases. The method comprises administering to said patient a therapeutically effective amount of both a N-alkyl derivative of deoxynojirimycin (DNJ) and a glucocerebrosidase enzyme to alleviate or inhibit the glycolipid storage disease. The alkyl group has from about two to about 20 carbon atoms and preferably is butyl, nonyl or decyl.

9 Claims, 6 Drawing Sheets

COMBINATION DRUG THERAPY FOR GLYCOLIPID STORAGE DISEASES

This is a Continuation of Application Ser. No. 09/620,026, filed Jul. 20, 2000, and claims the benefit of provisional application 60/145,568 filed Jul. 26, 1999.

BACKGROUND OF THE INVENTION

The present invention relates to combination drug therapy for the treatment of Gaucher's disease and other glycolipid storage diseases.

Gaucher's disease is a glycolytic storage disease caused by a genetic deficiency in activity of the catabolic enzyme beta-glucocerebrosidase. Beutler, *Proc. Natl. Acad. Sci. USA.* 90, 5384–5390 (1993). Manifestations of this disease are impaired hematopoiesis, bone fractures, a thinning of the bone cortex and massive enlargement of the spleen and liver.

In recent years, several therapies have been proposed for the treatment of Gaucher's disease. An early therapeutic approach involved replacement of the deficient enzyme. See, for example, Dale and Beutler, *Proc. Natl. Acad. Sci. USA* 73, 4672–4674 (1976); Beutler et al., *Blood* 78, 1183–1189 (1991); and Beutler, *Science* 256, 794–799 (1992).

Leading commercial products for enzyme replacement are CEREDASE (glucocerebrosidase), which is derived from human placental tissues, and CEREZYME (recombinant human glucocerebrosidase), both of which are produced by Genzyme Corp. See, for example, U.S. Pat. Nos. 3,910,822; 5,236,838; and 5,549,892. See also U.S. Pat. Nos. 5,879,680 and 6,074,684 on cloned DNA for synthesizing human glucocerebrosidase.

Conjugates of the glucocerebrosidase enzyme with polyethylene glycol (PEG) have also been advanced by Enzon Inc. for treatment of Gaucher's disease. See, for example, U.S. Pat. Nos. 5,705,153 and 5,620,884.

Still another approach for treatment of the disease is gene therapy, which involves an ex vivo gene transfer protocol. See, for example, U.S. Pat. No. 5,911,983.

Another recent approach involves administration of the totally synthetic drugs, N-butyldeoxynojirimycin and N-butyldeoxygalactonojirimycin, as described, respectively, by Platt et al., *J. Biol. Chem.* 269, 8362–8365 (1994); Id. 269, 27108–27114 (1994). See also, U.S. Pat. Nos. 5,472,969; 5,786,368; 5,798,366; and 5,801,185.

N-butyldeoxynojirimycin (N-butyl-DNJ) and related N-alkyl derivatives of DNJ are known inhibitors of the N-linked oligosaccharide processing enzymes, α-glucosidase I and II. Saunier et al., *J. Biol. Chem.* 257, 14155–14161 (1982); Elbein, *Ann. Rev. Biochem.* 56, 497–534 (1987). As glucose analogs, they also have potential to inhibit glycosyltransferases. Newbrun et al., *Arch. Oral Biol.* 28, 516–536 (1983); Wang et al., *Tetrahedron Lett.* 34, 403–406 (1993). Their inhibitory activity against the glycosidases has led to the development of these compounds as antihyperglycemic agents and as antiviral agents. See, e.g., PCT Int'l. Appln. WO 87/030903 and U.S. Pat. Nos. 4,065,562; 4,182,767; 4,533,668; 4,639,436; 5,011,829; 5,030,638; and 5,264,356.

In particular, N-butyl-DNJ has been developed as an inhibitor of human immunodeficiency virus (HIV) as described by Fleet et al., *FEBS Lett.* 237, 128–132 (1988), and by Karpas et al., *Proc. Nat'l. Acad. Sci. USA* 85, 9229–9233 (1988), U.S. Pat. No. 4,849,430; and as an inhibitor of hepatitis B virus (HBV) as described by Block et al., *Proc. Natl. Acad. Sci. USA* 91, 2235–2239 (1994), PCT Int'l. Appln. WO 95/19172 and U.S. Pat. No. 6,037,351.

BRIEF DESCRIPTION OF THE INVENTION

In accordance with the present invention, a novel method and composition is provided for the treatment of a patient affected with Gaucher's disease or other such glycolipid storage diseases. The method of the invention comprises administering to said patient a therapeutically effective amount of both a N-alkyl derivative of 1,5-dideoxy-1,5-imino-D-glucitol having from about two to about 20 carbon atoms in the alkyl chain and a glucocerebrosidase enzyme. The N-alkyl substituent can be a short-chain alkyl group such as, e.g., ethyl, butyl or hexyl, or a long-chain alkyl group such as, e.g, nonyl, decyl, undecyl, dodecyl, tetradecyl, hexadecyl, octadecyl and eicosyl.

A therapeutically effective amount is meant an amount effective in alleviating or inhibiting Gaucher's disease or other such glycolipid storage diseases in said patient. The glucocerebrosidase provides enzyme replacement for non-breakdown of glucocerebroside and the N-alkyl-DNJ jointly provides glycolipid inhibitory action. By use of the combination drug therapy of the invention, the medical benefits of both types of drugs should accrue to the patient with reduced amounts of either or both drugs than otherwise necessary to obtain equivalent or enhanced therapeutic results. That is, an additive or synergistic effect can reduce the frequency of the administration of the glucocerebrosidase enzyme and lower the dose of the long-chain N-alkyl-DNJ otherwise required for monotherapy of the disease.

The alkyl group in the short-chain N-alkyl-DNJ compounds preferably contains four to six carbon atoms (e.g., butyl or hexyl). A most preferred compound is N-butyl-1,5-dideoxy-1,5-imino-D-glucitol, also known as the N-butyl derivative of deoxynojirimycin (DNJ), which also is abbreviated herein as N-butyl-DNJ.

The alkyl group in the long-chain N-alkyl-DNJ compounds preferably contains nine to ten carbon atoms (i.e., nonyl and decyl). A most preferred compound is N-nonyl-1,5-dideoxy-1,5-imino-D-glucitol, also known as the N-nonyl derivative of deoxynojirimycin (DNJ), which also is abbreviated herein as N-nonyl-DNJ.

In the field of general organic chemistry, the long-chain alkyl groups are known to provide more hydrophobic properties to compounds than are the short-chain alkyl groups. That is, solubility with water decreases with increase in chain length and decrease in temperature. For example, at 46° C., caproic acid (short-chain hexyl group) dissolves 10% by weight of water, whereas stearic acid (long-chain octadecyl group) dissolves only 0.92% even at the higher temperature of 69° C. *Bailey's Industrial Oil and Fat Products,* ed. Daniel Swern, 3d ed. 1964, p. 126.

The long-chain N-alkyl derivatives of DNJ are known amino-sugar compounds. They were originally described as members of a group of short-chain and long-chain N-alkyl derivatives of DNJ having both glucosidase I inhibitory activity and antiviral activity, although no data on the long-chain N-alkyl derivatives was disclosed. See, e.g., DE 3,737,523, EP 315,017 and U.S. Pat. Nos. 4,260,622; 4,639,436; and 5,051,407.

In another early study, although N-alkylation of the base DNJ reduced the concentration required for 50% inhibition of glucosidase I, the inhibitory activity was reduced as the length of the N-alkyl chain was increased from N-methyl to N-decyl according to Schweden et al., *Arch. Biochem. Biophys.* 248, 335–340, at 338 (1986).

As far as the antiviral activity of the amino-sugar compounds against any particular virus is concerned, the activity of any specific analog cannot be predicted in advance. For example, in biologic tests for inhibitory activity against the human immunodeficiency virus (HIV), slight changes in the structure of the N-substituent were shown to have pronounced effects upon the antiviral profile as reported by Fleet et al., *FEBS Lett.* 237, 128–132 (1988). As disclosed in U.S. Pat. No. 4,849,430, the N-butyl derivative of DNJ was unexpectedly found to be more than two log orders more effective as an inhibitor of HIV than the N-methyl analog and three log orders more effective than the N-ethyl analog.

In another study of N-alkyl derivatives of DNJ for activity against glycolipid biosynthesis, the N-hexyl derivative of DNJ required a dose of 0.2 mg/ml, whereas the corresponding N-butyl analog required a dose of only 0.01–0.1. On the other hand, the N-methyl analog was inactive. Thus, it was believed that effective carbon chain length of the N-alkyl group for this activity ranged from 2 to 8 according to U.S. Pat. No. 5,472,969. No disclosure was made therein concerning the N-nonyl or other long-chain N-alkyl derivatives of DNJ.

N-nonyl-DNJ has been reported to be effective as an inhibitor of the Hepatitis B virus (HBV) based on inhibition of alpha-glucosidases in the cellular endoplasmic reticulum (ER) according to Block et al., *Nature Medicine* 4(5) 610–614 (1998).

The effectiveness of the long-chain N-alkyl derivatives of DNJ in the method of the invention for treatment of Gaucher's disease and other such glycolipid storage diseases is illustratively demonstrated herein by inhibitory activity of N-nonyl and N-decyl DNJs against glycolipid biosynthesis in Chinese hamster ovary (CHO) cells and human myeloid (HL-60) cells.

CHO cells are well-known glycoprotein-secreting mammalian cells. A typical CHO cell line is CHO-K1 which is available to the public from the American Type Culture Collection, Bethesda, Md., under accession number ATCC CCL 61.

HL-60 cells are human promyelocytic cells described by Collins et al., *Nature* 270, 347–349 (1977). They are also readily available from the American Type Culture Collection under accession number ATCC CCL 240.

Effective activity of N-nonyl-DNJ also is further illustratively demonstrated herein in conventional bovine kidney cells (e.g., MDBK, ATCC CCL 22) and hepatoma cells (e.g., HepG2, ATCC HB 8065).

The unpredictability of the N-nonyl-DNJ against glycolipid biosynthesis is demonstrated herein by its inhibitory activity in the foregoing two cell lines. The N-nonyl-DNJ was unexpectedly found to be from about ten- to about twenty-fold better in the CHO cells and about four hundred times better in the HL-60 cells than N-butyl-DNJ at equivalent concentrations. The N-decyl-DNJ was demonstrated to be an effective inhibitor in HL-60 cells at 50 times lower concentrations than N-butyl-DNJ. These results were further unexpected in view of the increased hydrophobic nature of the long-chain N-alkyl derivatives of DNJ.

The N-nonyl-DNJ also exhibits a more dramatic difference than N-butyl-DNJ in uptake which permits its use at a substantially lower level. In tests of organ distribution, the N-nonyl-DNJ was taken up five times better into the brain than N-butyl-DNJ. Thus, the N-nonyl-DNJ is believed to be a substantially better compound than N-butyl-DNJ for treating glycolipid storage disorders which involve the non-systemic side.

N-nonyl-DNJ and N-decyl-DNJ can be conveniently prepared by the N-nonylation or N-decylation, respectively, of 1,5-dideoxy-1,5-imino-D-glucitol (DNJ) by methods analogous to the N-butylation of DNJ as described in Example 2 of U.S. Pat. No. 4,639,436 by substituting an equivalent amount of n-nonylaldehyde or n-decylaldehyde for n-butylaldehyde. The starting materials are readily available from many commercial sources. For example, DNJ is available from Sigma, St. Louis, Mo., whereas n-nonylaldehyde, also known as 1-nonanal or pelargonaldehyde, and n-decylaldehyde, also known as decanal, are commercially available from Aldrich, Milwaukee, Wis. It will be appreciated, however, that the N-alkyl-DNJ used in this combination drug therapy is not limited to any particular method of synthesis of the N-butyl-DNJ, N-nonyl-DNJ, N-decyl-DNJ, or other N-alkyl derivatives of DNJ.

The glucocerebrosidase used in the combination drug therapy also is a known drug as described above. For example, it can be derived from human placental tissue by conventional isolation and purification techniques or prepared by recombinant DNA procedures. Conventional methods of isolation and purification from human placental tissue are described By Dale and Beutler, *Proc. Natl. Acad. Sci. USA* 73, 4672–4674 (1976) and in U.S. Pat. No. 3,910,822. Suitable methods of production by recombinant DNA are described in U.S. Pat. Nos. 5,236,838, 5,549,892 and 5,879, 680. The glucocerebrosidase can also be conjugated with carrier molecules such as, for example, polyethylene glycol (PEG) as described in U.S. Pat. Nos 5,705,153 and 5,620, 884. It will be appreciated, however, that the glucocerebrosidase used in the combination drug therapy is not limited to any particular method of production.

The N-butyl-DNJ, N-nonyl-DNJ, N-decyl-DNJ, and other N-alkyl derivatives of DNJ, can be used for treatment of patients afflicted with Gaucher's disease and other glycolipid storage diseases by conventional methods of administering therapeutic drugs. Thus, the active compound is preferably formulated with pharmaceutically acceptable diluents and carriers. The active drug can be used in the free amine form or the salt form. Pharmaceutically acceptable salt forms are illustrated, e.g., by the HCl salt. The amount of the active drug to be administered must be an effective amount, that is, an amount which is medically beneficial against Gaucher's disease or other glycolipid storage disease but does not present adverse toxic effects which overweigh the advantages that accompany its use.

It would be expected that the adult human daily dosage would normally range from about 0.1 to about 1000 milligrams of the active compound. The preferable route of administration is orally in the form of capsules, tablets, syrups, elixirs, gels and the like, although parenteral administration also can be used.

The glucocerebrosidase enzyme likewise can be administered by conventional means, preferably by intravenous infusion, e.g. administration of the active enzyme in a pharmaceutically acceptable carrier such as physiological saline. Initially, a dose of about 60 U per kilogram of body weight every two weeks was recommended. See, e.g., Beutler, *Science* 256, 794–799 (1992). After 6 to 12 months of therapy, doses of 7.5 to 15 U per kilogram every two weeks were suggested according to Moscicki et al., *New Engl. J. Med.* 328, 1564 (1993).

Illustratively, the two combination drug components can be administered together or separately, e.g., administration of the enzyme by periodic administration (e.g., weekly or bimonthly) and oral administration of the N-alkyl-DNJ daily.

By use of the combination drug therapy described herein, an additive or synergistic effect can be obtained to reduce the aforesaid frequency of the intravenous injection of the glucocerebrosidase and lower the dose of the N-alkyl-DNJ otherwise required for monotherapy of Gaucher's disease.

Suitable formulations of the active components in pharmaceutically acceptable diluents and carriers in therapeutic dosage from can be prepared by the person skilled in the art by reference to general texts and treatises in the pharmaceutical field such as, for example, Remington's Pharmaceutical Sciences, Ed. Arthur Osol, 16 ed., 1980, Mack Publishing Co. Easton, PA., and 18th ed., 1990.

Other glycolipid storage diseases to which the method of the invention is directed are, e.g., Tay-Sachs disease, Sandhoff disease, Fabry disease, GM1 gangliosidosis and fucosidosis.

DETAILED DESCRIPTION OF THE INVENTION

While the specification concludes with claims particularly pointing out and distinctly claiming the subject matter regarded as forming the invention, it is believed that the invention will be better understood from the following preferred embodiments of the invention taken in conjunction with the accompanying drawings.

BRIEF DESCRIPTION OF THE DRAWINGS

a) control, no compound
  b) 50 $\mu$M NB-DNJ
  c) 5 $\mu$M NB-DNJ
  d) 2.5 $\mu$M NB-DNJ
  e) 0.25 $\mu$M NB-DNJ
  f) 0.0025 $\mu$M NB-DNJ
  g) 50 $\mu$N NB-DNJ
  h) 5 $\mu$N NB-DNJ
  i) 2.5 $\mu$N NB-DNJ
  j) 0.25 $\mu$N NB-DNJ
  k) 0.0025 $\mu$N NB-DNJ After extraction the radioactively labelled glycolipids were separated by TLC and visualized by radioautography. NB-DNJ is N-butyl-DNJ. NN-DNJ is N-nonyl-DNJ

(a) Ceramide structure from the crystal structure of glucosylceramide. The acceptor hydroxyl is on $C1^1$.
  (b) The structure NB-DNJ (N-alkyl) based on NMR studies and molecular modelling.
  (c) One possible overlay of ceramide and NB-DNJ.

FIG. 5 is a bar graph of estimated radioactivity. Radiolabelled N-butyl-DNJ and N-nonyl-DNJ were added to cultured CHO, MDBK and HepG2 cells for the times (hours) indicated. Cells were extensively washed and acid precipitated. After solution in NaOH, cell associated radioactivity was determined as a percentage of radiolabelled compound added.

FIG. 6 is a bar graph which shows organ distribution of radiolabelled N-butyl-DNJ (NB-DNJ) and N-nonyl-DNJ (NN-DNJ). Mouse body fluids and organs were collected for different times (30, 60, 90 minutes) after gavage with radiolabelled compound. Radioactivity in each sample was determined and expressed as a percentage of radioactivity recovered. Solid bars, NN-DNJ, hatched bars, NB-DNJ.

In order to illustrate the invention in greater detail, the following specific laboratory examples are carried out. Although specific examples are thus illustrated herein, it will be appreciated that the invention is not limited to these specific, illustrative examples or the details therein.

EXAMPLE I

A comparison was made between N-butyl-DNJ and N-nonyl-DNJ for glycolipid biosynthesis inhibition which showed that potency is cell and chain length dependent. Chinese Hamster Ovary (CHO) cells and human myeloid (HL-60) cells grown in the presence of varying concentrations of inhibitor in addition to a precursor (radiolabelled palmitic acid) of glycolipid biosynthesis were treated with solvents to extract the glycolipids by the procedure described by Platt et al., J. Biol. Chem. 269, 8362–8365 (1994).

Figure 1A:
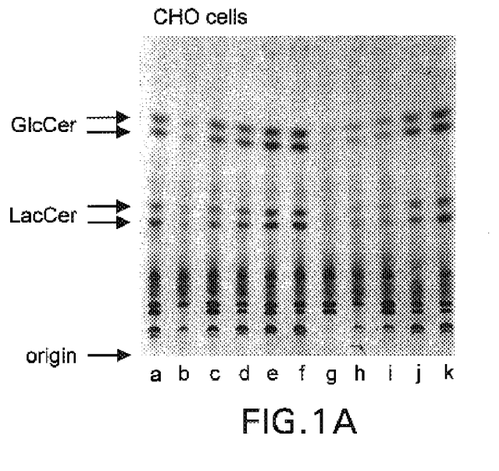
FIG. 1 shows thin layer chromatography of (a) CHO and (b) HL-60 treated cells. Cells were cultured for four days in the presence of radiolabelled palmitic acid and the following concentrations of compound.
Figure 1B:
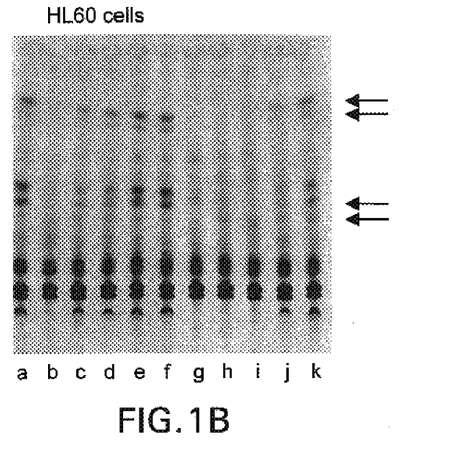

The radiolabelled lipids were separated by TLC (FIG. 1) and bands corresponding to glucosylceramide and lactosylceramide were quantitated by scanning densitometry to estimate the reduction in glycolipid biosynthesis. These data were plotted to obtain inhibitory constants ($IC_{50}$) for both cell lines and compounds (Table 1).

These data show that cell lines have different sensitivities to both N-butyl- and N-nonyl-DNJ. HL-60 cells are more than 10 times more sensitive to N-butyl-DNJ and 100 times more sensitive to N-nonyl-DNJ than CHO cells. This cell specificity is unexpected. In addition, N-nonyl is between 10 and 365 times more effective than N-butyl-DNJ.

Figure 2A:
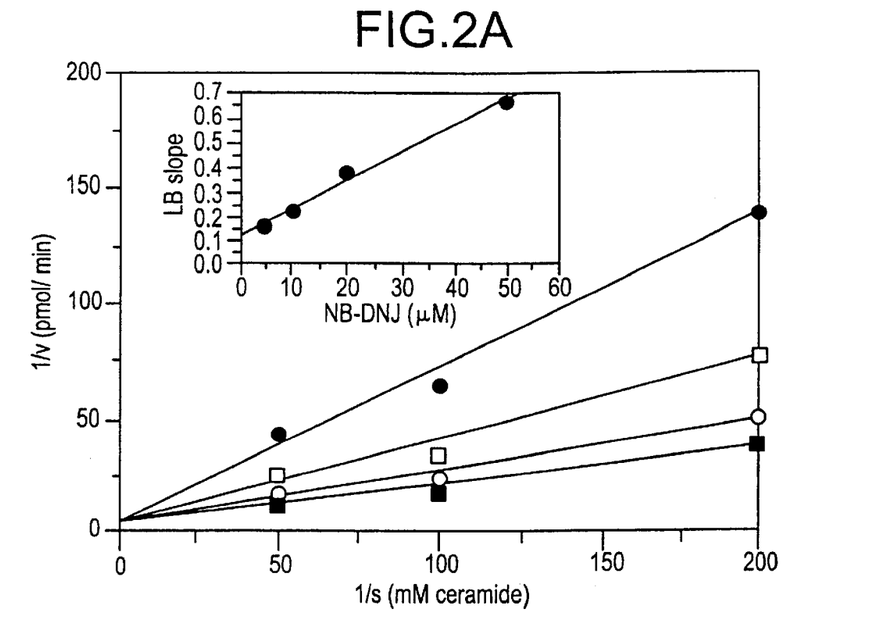
FIG. 2 shows double reciprocal plots of the inhibition of the ceramide glucosyltransferase by N-butyl-DNJ (NB-DNJ). HL-60 cell ceramide glucosyltransferase activity was measured using (a) ceramide concentrations of 5–20 $\mu$M and (b) UDP-glucose concentrations of 0.59–5.9 $\mu$M. NB-DNJ concentrations of 5–100 $\mu$M were used. The inhibition constants ($K_i$) were calculated by plotting the Lineweaver-Burk slope against inhibitor concentration as shown in the inserts.
Figure 2B:
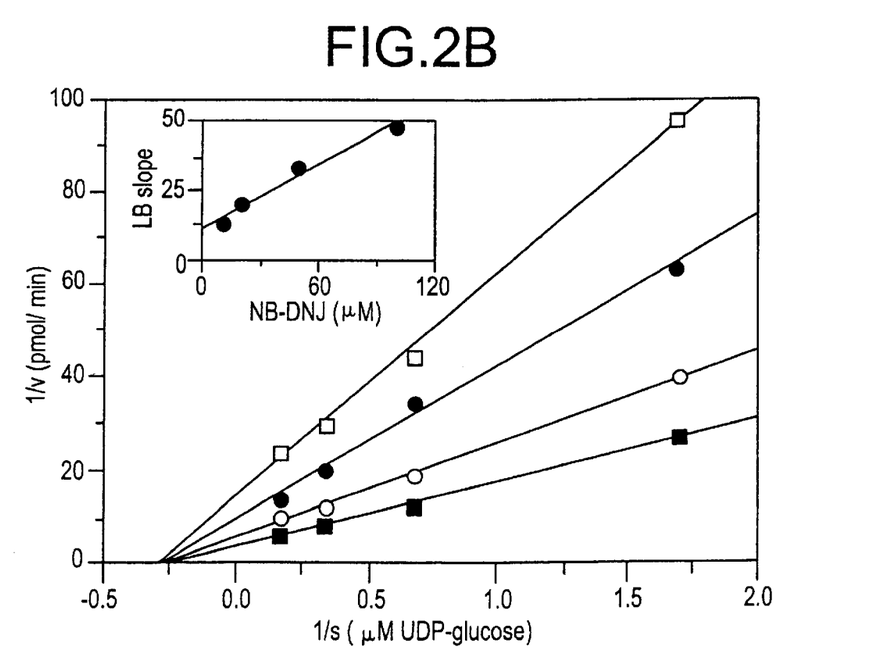
Figure 3:
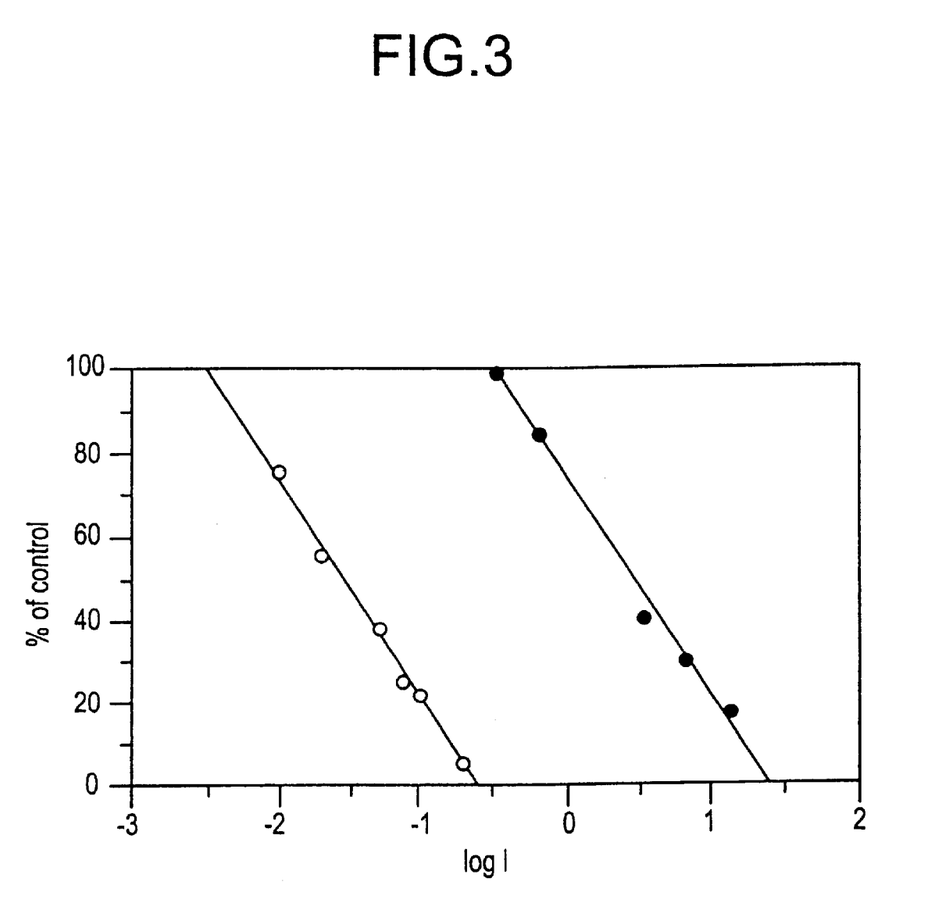
FIG. 3 shows inhibition of HL-60 cell ceramide glucosyltransferase activity by N-butyl-DNJ (open circles) and N-nonyl-DNJ (closed circles). Activity was expressed as a percentage of control without inhibitor and the $IC_{50}$ values calculated from the rate curves shown. N-butyl-DNJ=27.1 $\mu$M; N-nonyl-DNJ=2.8 $\mu$M.

Detailed work to probe the kinetics of inhibition of the ceramide glucosyltransferase, the enzyme inhibited by alkylated deoxynojirimycin compounds, has demonstrated that these compounds are competitive inhibitors for ceramide and non-competitive inhibitors for UDP-glucose (FIG. 2). N-nonyl-DNJ has a 10-fold increased potency over N-butyl-DNJ in inhibiting ceramide glucosyltransferase in in vitro assays ($IC_{50}$ values of 2.8 $\mu$M and 27.1 $\mu$M respectively, see FIG. 3).

Figure 4A:
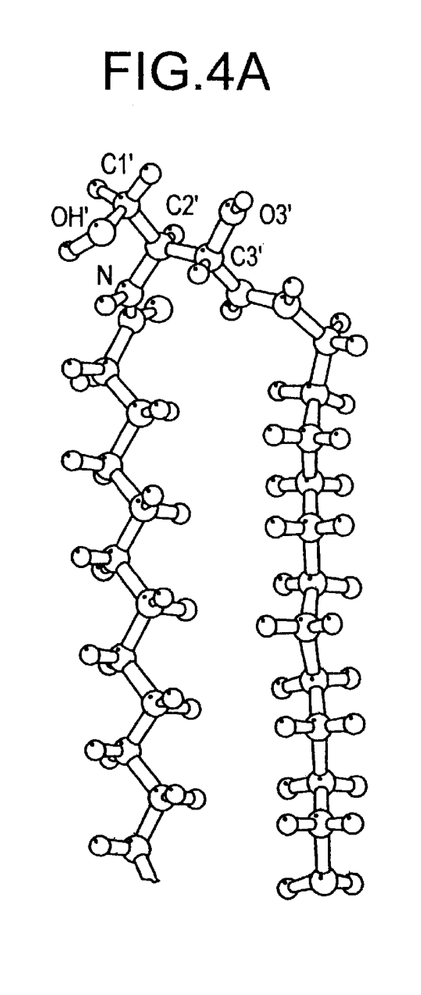
FIG. 4 shows structural relationship between NB-DNJ and ceramide glucosyltransferase substrate.
Figure 4B:
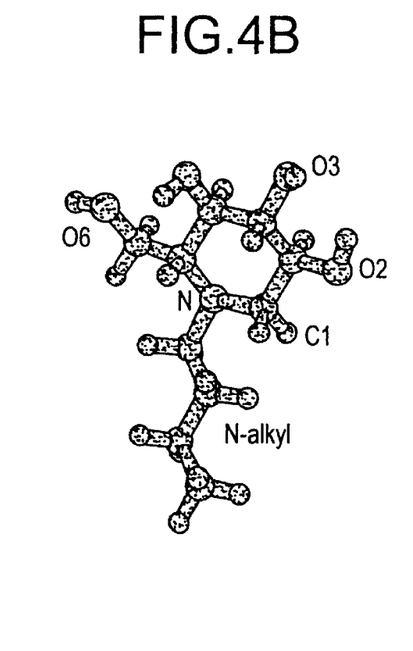
Figure 4C:
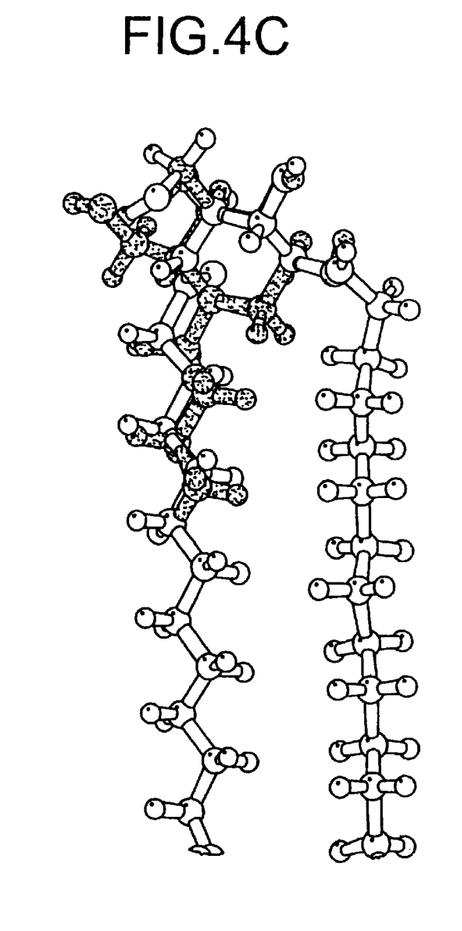

The mechanism of action of alkylated deoxynojirimycin compounds is proposed to be that of ceramide mimicry and a model demonstrating this mimicry at the molecular level is shown in FIG. 4. An energy minimized molecular model of NB-DNJ and ceramide predicts structural homology of three chiral centers and the N-alkyl chain of NB-DNJ, with the trans-alkenyl and N-acyl chain of ceramide. This increased in vitro potency does not explain the dramatic difference in inhibition of glycolipid biosynthesis in cellular systems.

The activity is explained by the differential uptake into cells. In three cell lines, CHO, MDBK and HepG2, radiolabelled N-nonyl-DNJ and N-butyl-DNJ were incubated for up to 24 hours and the amount of cell-associated radioactivity determined. In all cases N-nonyl-DNJ was increased by 3.5–5.0 fold. It is clearly the combination of the inhibitory effect and increased uptake that is important in potentiating the inhibition by N-nonyl-DNJ.

Figure 5A:
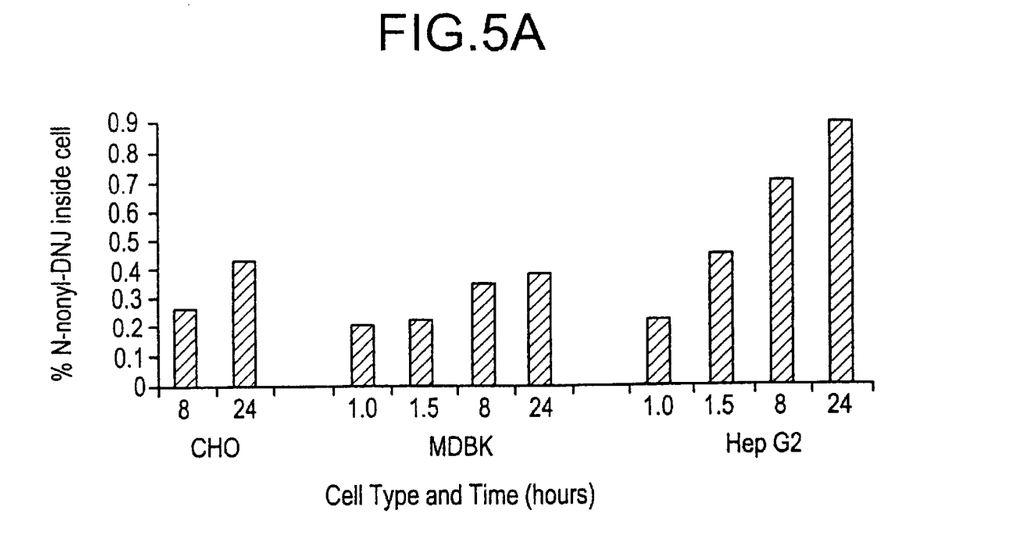
Figure 5B:
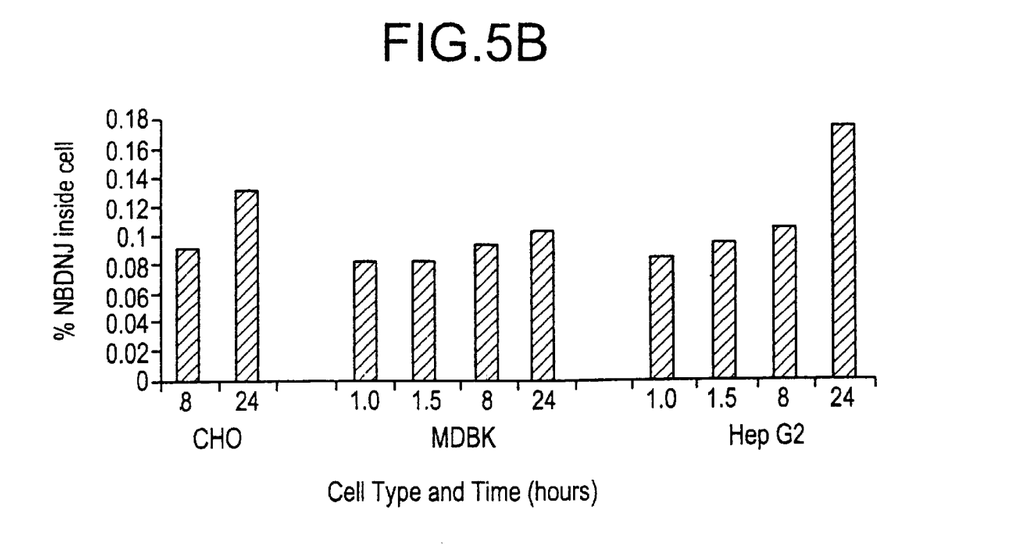
Figure 6:
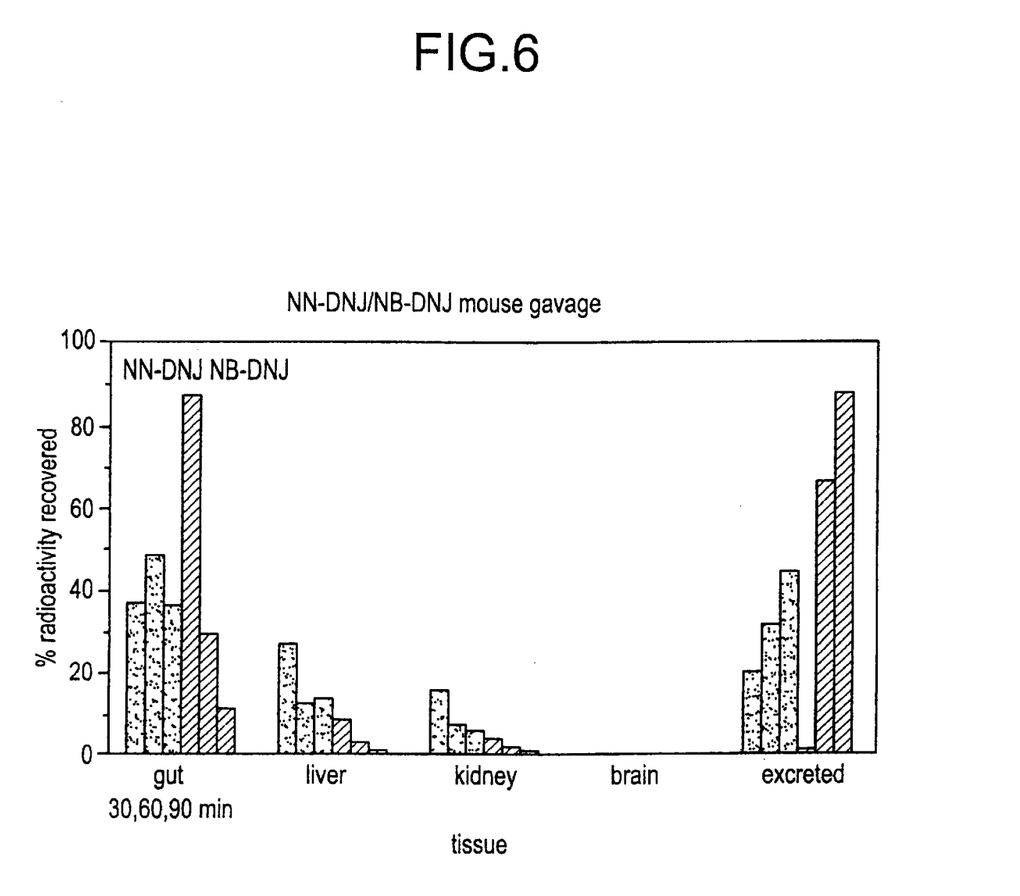

Further evidence that longer alkyl chains are taken up much better than the shorter alkyl chains has been obtained by in vivo studies with mouse. After oral gavage with radiolabelled N-nonyl-DNJ and N-butyl-DNJ for 30, 60, and 90 minutes, the body fluids were collected and organs removed for estimations of radioactivity (FIG. 5). The amount of radioactivity recovered in the liver and brain was 10 fold higher for N-nonyl-DNJ than N-butyl-DNJ after 90 min (see Table 2).

Evidence was obtained that longer (than C9) chain DNJ compounds are more effective ceramide glucosyltransferase inhibitors. This follows from proposed mechanism of action studies that demonstrate enhanced potency correlates with ceramide mimicry (FIG. 4). More specifically, N-decyl-DNJ (C10) shows inhibition at 50 times lower concentrations than N-butyl-DNJ in the HL-60 cell-based assay described above. In view of the above data, the long-chain N-alkyl derivatives of DNJ are more effective for treatment of glycolipid storage diseases.

TABLE 1

| Cells | N-butyl-DNJ ($IC_{50}$, $\mu M$) | N-nonyl-DNJ ($IC_{50}$, $\mu M$) |
| --- | --- | --- |
| CHO | 25–50 | 2–2.7 |
| HL-60 | 1.8–7.3 | 0.02–0.4 |

Table 1. Inhibition of glycolipids by N-butyl- and N-nonyl-DNJ. Radiolabelled glucosylceramide and lactosylceramide bands from FIG. 1 were quantitated by scanning densitometry and the percentage of control (no treatment, track a, FIG. 1) expressed in comparison to compound dose. From the linear curve, an $IC_{50}$ value was obtained. A range of values is quoted to represent variability of the radiolabelled products.

TABLE 2

| | % recovered N-nonyl-DNJ | | % recovered N-butyl-DNJ | |
| --- | --- | --- | --- | --- |
| Time (min) | Liver | Brain | Liver | Brain |
| 30 | 27.1 | 0.4 | 8.5 | 0.2 |
| 60 | 12.6 | 0.3 | 2.8 | 0.1 |
| 90 | 13.5 | 0.4 | 0.9 | 0.03 |

Table 2. Recovery of radiolabelled compounds after administration in the normal mouse. Mouse body fluids and organs were collected at different times after gavage with radiolabelled compound. Radioactivity in each sample was determined and expressed as a percentage of radioactivity recovered (data from FIG. 5).

EXAMPLE II

When the N-butyl-DNJ, N-nonyl-DNJ, N-decyl-DNJ or other N-alkyl-DNJ as defined herein is used in combination with the glycocerebrosidase enzyme for the treatment of Gaucher's disease or other such glycolipid storage disease, the medical benefits of both types of drugs accrue to the patient with reduced amounts of either or both drugs than otherwise necessary by monotherapy to obtain equivalent or enhanced therapeutic results. These therapeutic benefits are obtained with a dosage of about 0.1 to 1000 mg of the N-alkyl-DNJ and a dosage of about 7.5 to 60 U per Kg of body weight of the glucocerebrosidase enzyme.

One concern with combination therapy is that β-glucocerebrosidase is also inhibited by NB-DNJ. The $IC_{50}$ value is 520 $\mu M$ in an in vitro assay, 25 fold higher than that required to inhibit the ceramide glucosyltransferase activity ($IC_{50}$, 20.4 $\mu M$) (Platt et al., J. Biol. Chem. 269, 27108–27114, 1994). Therefore, the kinetic equilibrium for the metabolism of glucocerebroside in the presence of 5–50 $\mu M$ NB-DNJ will favor reduced substrate and not cause storage by inhibition of glucocerebrosidase (Platt, et al., id 1994). In practice, it is extremely difficult to sustain steady state serum concentrations in excess of 50 $\mu M$ NB-DNJ in orally dosed animals (Platt, et al., J. Biol. Chem. 272, 19365–19372, 1997). In the clinical trial of ND-DNJ a steady-state plasma concentration was achieved after 4–6 weeks of treatment. An oral dosing regime of 100 mg three times daily showed a peak plasma concentration of 6.8 $\mu M$ (1.5 $\mu g$/ml) (Cox et al., Lancet 355, 1481–1485, 2000).

However, in vivo the co-administration of NB-DNJ and glucocerebrosidase could lead to inhibition of enzyme activity and compromise potential combination therapy. It was therefore important to determine the kinetics of infused enzyme in mice treated with NB-DNJ. After five weeks of oral administration of NB-DNJ (4800 mg/Kg/day), sufficient to sustain a stable serum concentration of 50 $\mu M$ (Platt et al., id, 1997), mice were tail vein injected with Ceredase® at 5–10 U/Kg. Glucocerebrosidase activity was measured after injection using 4-methylumbelliferyl-β-glucoside as substrate and peak serum activity and half life for enzyme was calculated (TABLE 3).

TABLE 3

| Group (n) | Peak Activity (mU/ml) ± sem | Half Life (min) ± sem |
| --- | --- | --- |
| Untreated control (8) | 11.56 ± 3.11 | 2.079 ± 0.392 |
| NB-DNJ Treated (7) | 27.39 ± 7.24 | 3.361 ± 0.491 |

Table 3. Serum β-glucocerebrosidase activity in mice untreated or treated with 4800 mg/Kg/day NB-DNJ. Student's t-test was used to determine P-Values for activity and half life of enzyme in the two groups and were 0.076 and 0.064 respectively.

These data reveal that the infused β-glucocerebrosidase activity was not inhibited in the presence of NB-DNJ. An apparent elevation was observed, but due to the variability in the analysis this did not show statistical significance. One possible explanation for an apparent increase in activity is that exposure to low concentrations of imino sugar stimulated hydrolysis by stabilizing the active site. Other lysosomal enzymes are known to be stabilized by imino sugar inhibitors (Fan et al., Nature Med. 5, 112–115, 1999). The circulatory half life of the enzyme was found to be similar to previously published values (Friedman et al., Blood 93, 2807–2816, 1999).

However, in the presence of NB-DNJ the half life was extended, indicating that inhibitor protects enzyme from inactivation or reduces clearance by receptor mediated uptake (Friedman, et al., id, 1999).

The foregoing data thus suggest that the pharmacological profile of β-glucocerebrosidase would not be compromised in the presence of low concentrations of NB-DNJ, but can show improvement.

Various other examples will be apparent to the person skilled in the art after reading the present disclosure without departing from the spirit and scope of the invention. It is intended that all such other examples be included within the scope of the appended claims.

What is claimed is:

1. A method of treating a patient affected with a glycolipid storage disease comprising administering to said patient an effective amount of a combination of a N-alkyl derivative of deoxynojirimycin (DNJ) having from about two to about twenty carbon atoms in the alkyl chain and a glucocerebrosidase enzyme in synergistic proportions of reduced amounts of either or both said N-alkyl derivative of DNJ and said glucocerebrosidase enzyme to obtain equal or enhanced alleviation or inhibition of said glycolipid storage disease compared to monotherapy with either said N-alkyl derivative of DNJ or said glucocerebrosidase enzyme alone.

2. The method of claim 1 in which the N-alkyl derivative of deoxynojirimycin contains four to six carbon atoms in the alkyl chain.

3. The method of claim 2 in which the N-alkyl derivative of deoxynojirimycin is N-butyl-DNJ.

4. The method of claim 1 in which the N-alkyl derivative of deoxynojirimycin is N-nonyl-DNJ or N-decyl-DNJ.

5. The method of claim 4 in which the N-alkyl derivative of deoxynojirimycin is N-nonyl-DNJ.

6. The method of claim 1 in which the glycolipid storage disease is Gaucher's disease.

7. The method of claim 3 in which the glycolipid storage disease is Gaucher's disease.

8. The method of claim 5 in which the glycolipid storage disease is Gaucher's disease.

9. The method as in any one of claims 1–8, in which the N-alkyl derivative of deoxynojirimycin is administered in a dose of from about 0.1 to about 1000 mg and the glucocerebrosidase is administered in a dose of about 7.5 to about 60 U per kilogram of weight of said patient in a pharmaceutically acceptable diluent or carrier.

* * * * *

UNITED STATES PATENT AND TRADEMARK OFFICE
CERTIFICATE OF CORRECTION

PATENT NO. : 6,696,059 B2
DATED : February 24, 2002
INVENTOR(S) : Gary S. Jacob and Raymond A. Dwek It is certified that error appears in the above-identified patent and that said Letters Patent is hereby corrected as shown below:

Column 5,
Line 36, "f) 0.0025" should read -- f)0.025 --.
Line 37, "g)50 µN" should read -- g) 50 µM --.
Line 38, "h) 5 µN" should read -- h) 5 µM --.
Line 39, "i) 2.5 µN" should read -- i) 2.5 µM --.
Line 40, "j) 0.25 µN" should read -- j) 0.25 µM --.
Line 41, "k) 0.0025 µN" should read -- k) 0.025 µM --.

Signed and Sealed this

Fourteenth Day of September, 2004

JON W. DUDAS
*Director of the United States Patent and Trademark Office*